United States Patent [19]

Takahashi et al.

[11] Patent Number: 5,293,874
[45] Date of Patent: Mar. 15, 1994

[54] MEASUREMENT OF TRANSMISSION VELOCITY OF PULSE WAVE

[75] Inventors: Masaaki Takahashi; Masatoshi Nishimura; Nobuaki Nakatsubo, all of Tokyo, Japan

[73] Assignee: Sankyo Company, Limited, Tokyo, Japan

[21] Appl. No.: 829,451

[22] Filed: Jan. 30, 1992

[30] Foreign Application Priority Data

Jan. 31, 1991 [JP] Japan .................. 3-031889

[51] Int. Cl.5 .............................. A61B 5/02
[52] U.S. Cl. ................... 128/687; 128/691
[58] Field of Search ........... 128/687, 688, 691, 693, 128/694, 715, 773

[56] References Cited

U.S. PATENT DOCUMENTS

| | | |
|---|---|---|
| 3,132,643 | 5/1964 | Baum et al. |
| 3,734,086 | 5/1973 | Phelps, Sr. ............ 128/687 |
| 4,245,648 | 1/1981 | Trimmer et al. |
| 4,546,777 | 10/1988 | Groch et al. ........... 128/715 |
| 4,557,270 | 12/1985 | John ................... 128/691 |
| 4,562,843 | 1/1986 | Djordjevich et al. .... 128/693 |
| 4,993,420 | 2/1991 | Welkowitz et al. ...... 128/691 |
| 5,033,472 | 7/1991 | Sato et al. ............ 128/691 |

FOREIGN PATENT DOCUMENTS 2281093 3/1976 France.

OTHER PUBLICATIONS

F. J. Callaghan et al. "Relationship Between Pulse-Wave Velocity and Arterial Elasticity", Medical & Biological Engineering & Computing, May 1986, pp. 248 to 254.

Primary Examiner—Lee S. Cohen
Assistant Examiner—Samuel Gilbert
Attorney, Agent, or Firm—Spencer, Frank & Schneider

[57] ABSTRACT

A device for measuring a transmission velocity of a pulse wave includes sensors for sensing heart sounds, and pulse wave signals at upstream and downstream sides of a blood flow. Analog to digital conversion circuitry, coupled to the sensors, converts signals from the sensors from analog to digital form. A data processor, coupled to the analog to digital conversion circuitry processes data received from the analog to digital conversion circuitry. A display device, coupled to the data processor, displays waveforms and numerical data received from the data processor. The data processor includes seven processing units. A first processing unit, coupled to the analog to digital conversion circuitry, detects a first heart sound and generates a marker signal. Second and third processing units, coupled to the analog to digital conversion circuitry, transform digital signals received from the analog to digital conversion circuitry into data for display. A fourth processing unit, coupled to the first, second, and third processing units, detects the marker signal from the first processing unit and obtains predetermined data from the data received from the second and third processing units. A fifth processing unit, coupled to the second and third processing units, temporarily stores data received from the second and third processing units. A sixth processing unit, coupled to the fourth processing unit, determines a transmission time of a pulse wave to derive a transmission velocity of the pulse wave. A seventh processing unit, coupled to the sixth processing unit, transforms signals from the sixth processing unit for display.

9 Claims, 10 Drawing Sheets

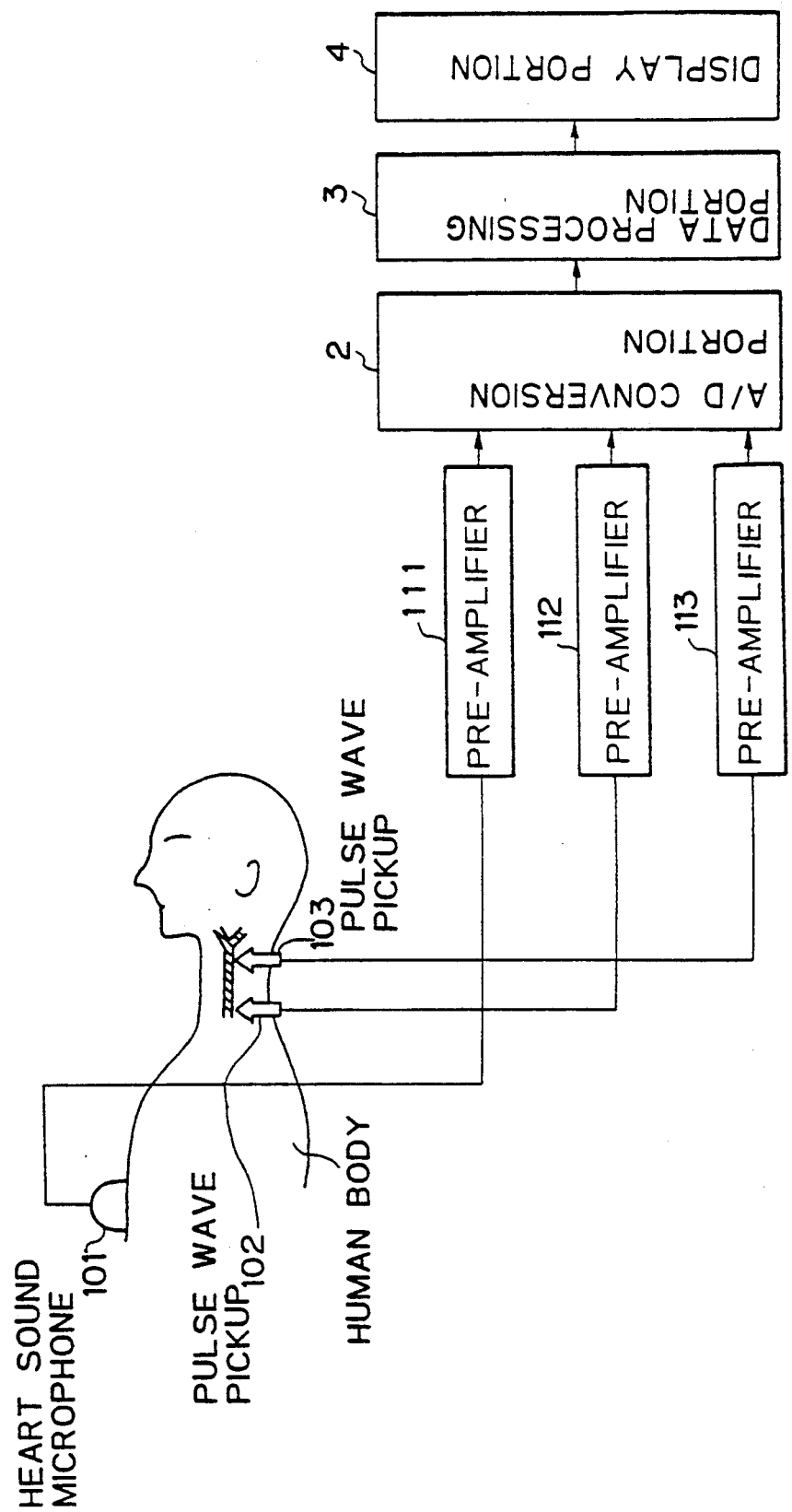

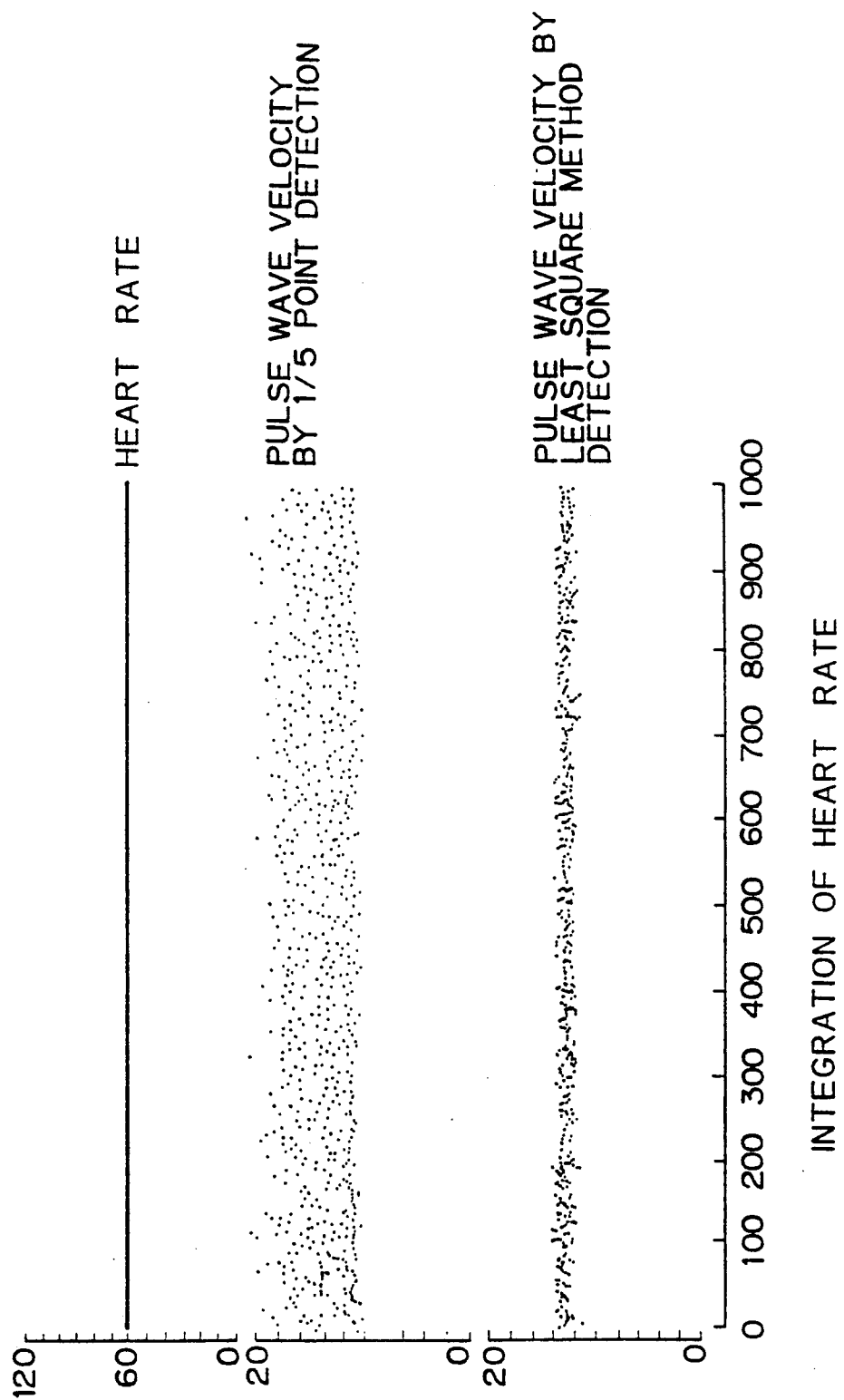

MEASUREMENT OF TRANSMISSION VELOCITY OF PULSE WAVE

BACKGROUND OF THE INVENTION

1. Field of the Invention

The present invention relates to an apparatus and a method of measuring the transmission velocity of a pulse wave. The method and apparatus according to the present invention are used for detecting the transmission velocity of a pulse wave in relation to the detection of the blood pressure and the elasticity of the tube wall of the artery of a human being.

2. Description of the Related Arts

In a report based on an investigation into the relationship between the degree of sclerosis of an artery and the pulse wave velocity (PWV), it was assumed that $C_o$ is the value of the pulse wave velocity, V is the volume of the artery, P is the internal pressure of the artery, $\rho$ is the density of the blood (regularly 1.055 g/cm$^3$), and V dP/dV is the bulk modulus (volumetric elasticity), the value of $C_o$ is represented by the formula $$C_o = \sqrt{(V/\rho) \cdot (dP/dV)} .$$

As a result it was found that, if the density of the blood is constant, the harder the tube wall of the artery, the higher the pulse wave velocity.

Also, it is known that the pulse wave velocity (PWV) in the aorta can be calculated based on detections of the pulse wave in the carotid artery, the pulse wave in the femoral artery, and the heart sound, using the formula $$PWV = 1.3L/(T+T_c).$$

In this equation, L represents the straight distance from the valve opening of the aorta to the femoral artery, T the time difference between the rising point of the pulse wave in the carotid artery and the rising point of the pulse wave in the femoral artery, and $T_c$ the time difference between the generation of the second sound, i.e., the sound of the closing of the aortic valve, of the heart sounds to the generation of the dip of the pulse wave, which is generated when the aortic valve is closed, in the carotid artery Accordingly, "$T+T_c$" is the time of a transmission of the pulse wave from the opening of the aortic valve to the femoral artery. The coefficient "1.3" is the correction coefficient of the actual length of the artery.

Recently, a demand has arisen for a precise measurement of the PWV over a relatively short distance, as the degree of the sclerosis of the tube wall of an artery in a relatively localized range can be detected by such a precise measurement of the PWV over a relatively short distance The detection of the localized existence of the sclerosis in the artery system, in association with the detection of the sclerosis in the entire artery system, is useful for the medical diagnosis and treatment of the vascular diseases accompanying sclerosis of the artery.

Since the carotid artery is located at the entrance of the cerebral blood vessel system, the degree of sclerosis of the tube wall of the carotid artery is considered to be as medically important as the heart artery system.

To achieve a precise measurement of the PWV over a relatively short distance, a measurement with a high time resolution is needed, since a very short transmission time on the order of milli-seconds through tens of milli-seconds of the PWV is estimated as the transmission time of the PWV over a short distance on the order of 5 cm.

In a prior art method of measuring the PWV, in which the PWV is obtained from a measurement of the time difference between 1/10 points or 1/5 points of the amplitudes of the rising parts of two pulse waves having a relatively stable pulse waveform, a problem arises in that the time difference is measured for only a single point, and if noise components are superposed on the pulse wave signal, tho amount of error in the time measurement is increased. Such an error cannot be neglected, particularly in the measurement of the PWV over a short distance on the order of 5 cm.

In another prior art method of measuring the PWV, in which the waveforms of the rising parts of two pulse waves are overlapped by using an analog delay element and the delay time therebetween is measured, a problem arises in that the process of the decision based on the overlap of the waveforms is carried out only by a visual fine adjustment of an oscilloscope by the operator, an automatic measurement of PWV for each heart beat cannot be made, only an averaged value is measured because the pulse wave signals for several heart beats are required for the overlapping of the waveforms, and the dynamic response characteristic for a load test, such as the test of an increase in pressure under cold temperature conditions, cannot be detected.

To obtain information on the background of the invention, refer to an article by F. J. Callaghan et al., "Relationship Between Pulse-Wave Velocity and Arterial Elasticity", Medical & Biological Engineering & Computing, May 1986, Pages 248 to 254.

SUMMARY OF THE INVENTION

An object of the present invention is to provide an improved apparatus and method of measuring the transmission velocity of a pulse wave, in which the measurement of the transmission velocity of the pulse wave over a relatively short distance can be carried out with a high precision, a real time measurement of the transmission velocity of the pulse wave in synchronization with the heart beat becomes possible, and an output of the result of an automatic measurement of the transmission velocity of the pulse wave, with a high precision, becomes possible.

According to the present invention, there is provided an apparatus for measuring a transmission velocity of a pulse wave, including: a sensor portion for sensing heart sounds, and pulse wave signals upstream and downstream of a blood flow; an analog to digital conversion unit for converting the signals from the sensor portion from an analog to a digital form; a data processing unit for processing data received from the analog to digital conversion unit; and a display unit for displaying waveforms and numerical data received from the data processing unit. The data processing unit includes a first processor for detecting the first heart sound and generating a marker signal; second and third processors for transforming the received signals for a display thereof; a fourth processor responsive to signals from the first, second, and third processors and detecting the marker signal to thereby obtain predetermined data from the data received; a fifth processor for receiving signals from the second and third processors and temporarily storing the received signals; a sixth processor for receiving a signal from the fourth processor and measuring the transmission time of the pulse wave to thereby derive the transmission velocity of the pulse wave; and a seventh processor for receiving a signal from the sixth processor and transforming the received signal for a display thereof.

According to the present invention, there is also provided a method of measuring the transmission velocity of a pulse wave, including the steps of: receiving a heart sound signal, and pulse wave signals upstream and downstream of a blood flow; detecting a first sound from the received heart sound signal; obtaining a pulse wave signal upstream and a pulse wave signal downstream, based on a first sound of the received heart sound signal; detecting a comparison reference point based on the first sound of the received heart sound and the pulse wave signals upstream and downstream side; carrying out a waveform coincidence processing for the pulse wave signals upstream and downstream and, based on the waveform coincidence processing, measuring the transmission time of the pulse wave; and deriving the transmission velocity of the pulse wave using the measured transmission time of the pulse wave.

BRIEF DESCRIPTION OF THE DRAWINGS

FIG. 2 illustrates the operation of an apparatus for measuring the transmission velocity of a pulse wave according to an embodiment of the present invention;

FIG. 9 shows examples of the actual detection of the transmission velocity of the pulse wave.

DESCRIPTION OF THE PREFERRED EMBODIMENTS

Figure 1A:
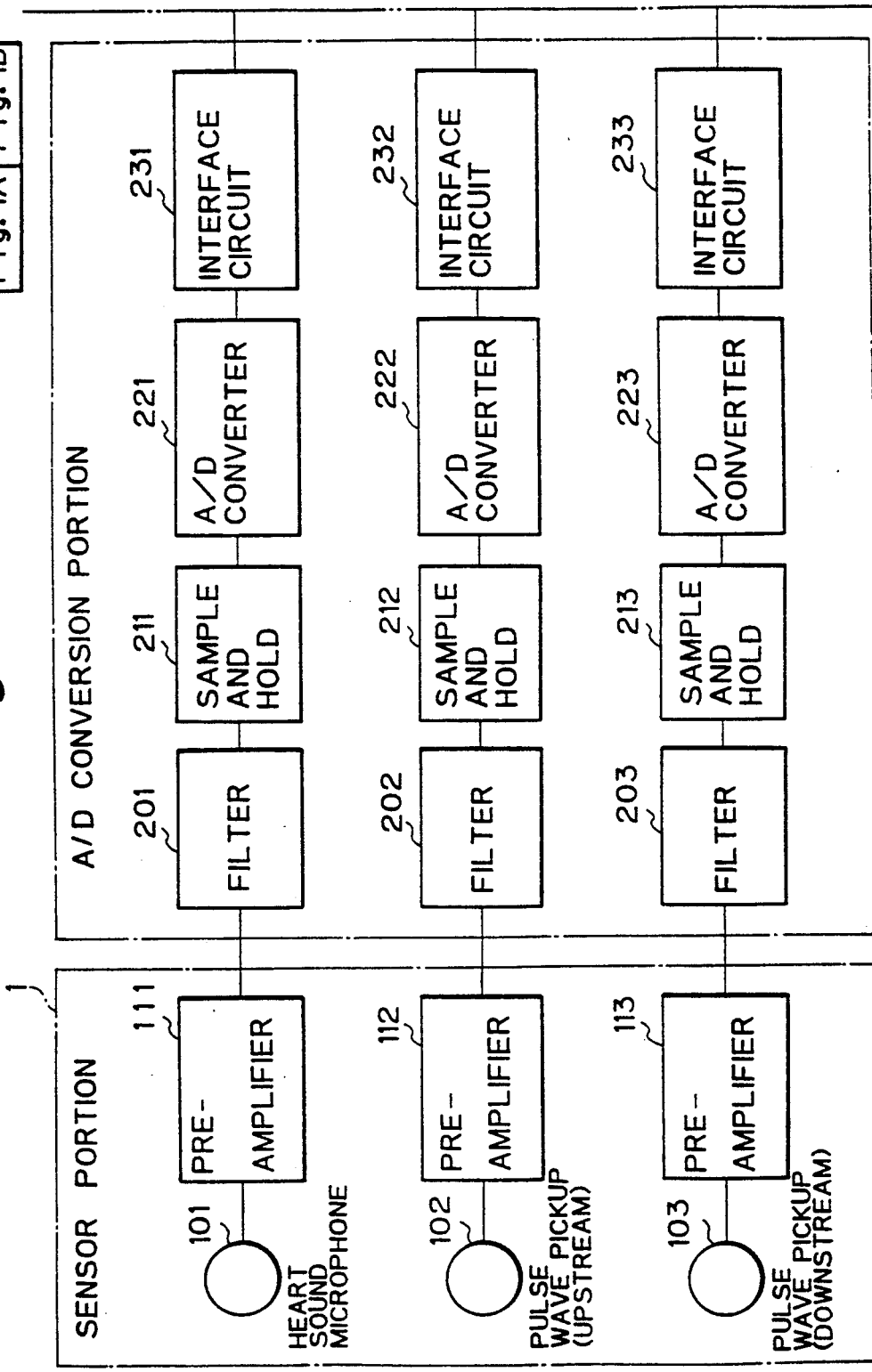
FIGS. 1A and 1B are a schematic diagram of an apparatus for measuring the transmission velocity of a pulse wave according to an embodiment of the present invention.
Figure 1B:
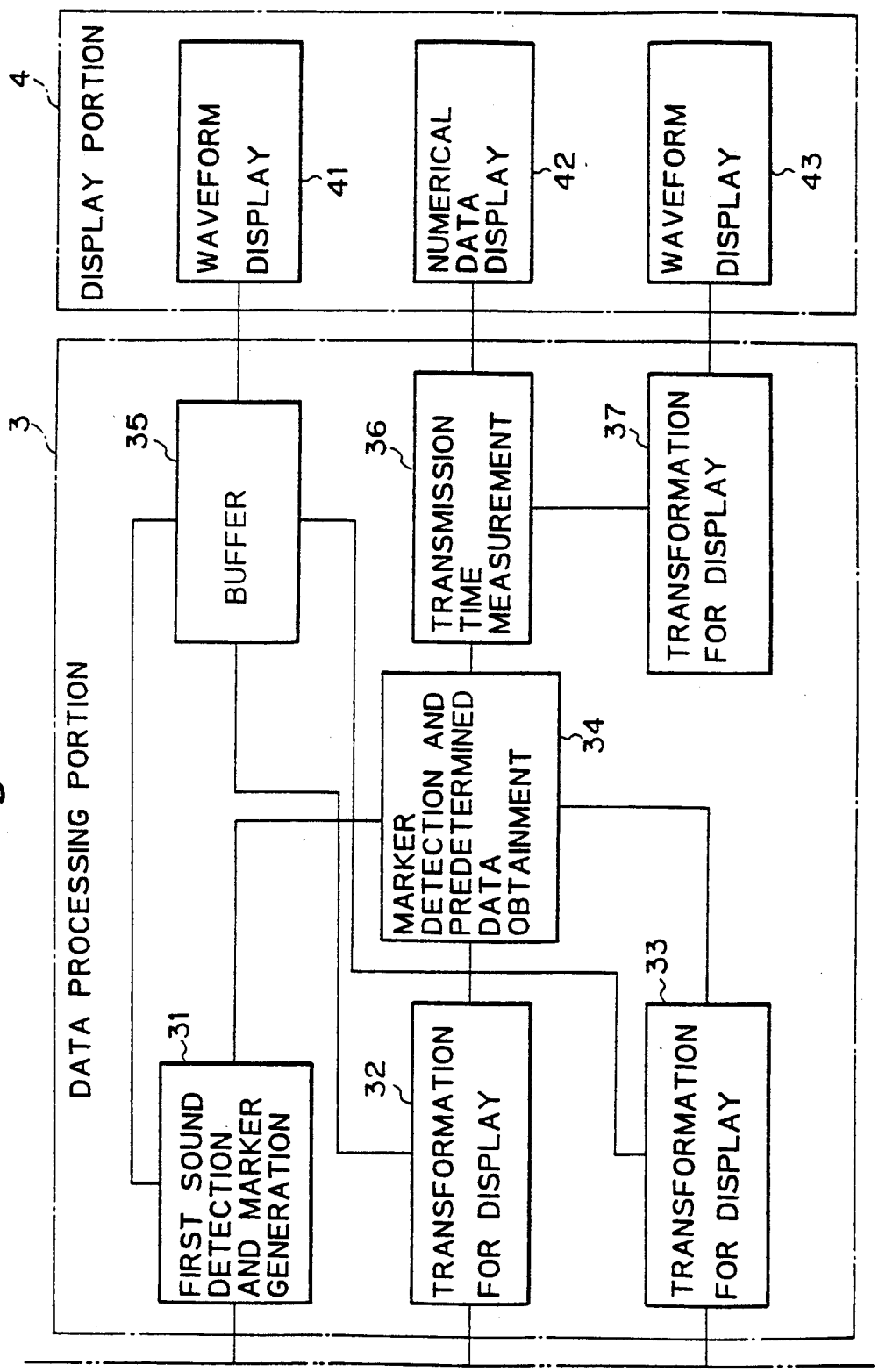

A schematic diagram of an apparatus for measuring the transmission velocity of a pulse wave according to an embodiment of the present invention is shown in FIG. 1 and the operation of this apparatus is illustrated in FIG. 2.

The apparatus shown in FIG. 1 is constituted by a sensor portion 1, an analog to digital conversion portion 2, a data processing portion 3, and a display portion 4. The sensor portion 1 includes a heart sound microphone 101, a pulse wave pickup 102 for the upstream side, a pulse wave pickup 103 for the downstream side, and pre-amplifiers 111, 112, and 113. The analog to digital conversion portion 2 includes filters 201, 202, and 203, sample and hold circuits 211, 212, and 213, analog to digital converters 221, 222, and 223, and interface circuits 231, 232, and 233. The data processing portion 3 includes a processor 31 for the first sound detection and the marker generation, a processor 32 for a transformation for a display thereof, a processor 33 for a transformation for a display thereof, a processor 34 for the marker detection and the predetermined data obtainment, a processor 35 as a buffer, a processor 36 for the transmission time measurement, and a processor 37 for a transformation for a display thereof The display portion 4 includes waveform display units 41 and 43 and a numerical data display unit 42.

The measurement of the transmission velocity of the pulse wave over a range of about 5 cm to 8 cm of the carotid artery and the radial artery and the finger tip portion is illustrated in FIG. 2. In the figure, the heart sound microphone 101, pulse wave pickup 102 for the upstream side of the blood flow, and pulse wave pickup 103 for the downstream side of the blood flow are mounted on a human body as a biological object. The signals from the microphone 101 and the pickups 102 and 103 are supplied to pre-amplifiers 111, 112, and 113, and the signals from the pre-amplifiers 111, 112, and 113 are supplied to the analog to digital conversion portion 2. The signals from the interface circuits 23 in the analog to digital conversion portion 2 are supplied to the data processing portion 3, and the signals from the processor 35, transmission time measurement unit 36, and transmission for display unit 37 in the data processing portion 3 are supplied to the display portion 4.

A photo-electric sensor having a peak sensitivity wavelength at infra-red range, or a scattered light detection type sensor with an infra-red light emitting diode, or the like, may be used for the pulse wave sensor. Also, a sensor in which minor variations of the skin surface are absorbed by a rubber balloon and a change in the pressure in the rubber balloon is detected by a semiconductor pressure sensor, or a piezoelectric film sensor, or the like, may be used, for the pulse wave sensor.

The conversion process in the analog to digital conversion portion 2 is such that a 16 bit resolution is provided for plus/minus 10 volts, and a sampling rate of 50 kHz is provided.

In the data processing portion 3, each of the processors 31 to 37 may be a functional element called "Transputer". The "Transputer" may be the T800, 20 MHz type.

In the processor 31, the signal from the interface circuit 231 is received, the first of the heart sounds is detected, the marker signal of 10 volts or the like is superposed on the received signal during a time of several tens of msec, and the produced signal is transmitted as a unit of 1000 data to the processor 34.

In the processor 32, the signal from the interface circuit 232 is received, the received data is transformed for a real time display of the waveform of the pulse wave at the upstream side, the transformed data is transmitted to the processor 35, and the received data is transmitted as a unit of 1000 data to the processor 34.

In the processor 33, the signal from interface circuit 233 is received, the received data is transformed for a real time display of the waveform of the pulse wave at the downstream side, the transformed data is transmitted to the processor 35, and the received data is transmitted as a unit of 1000 data to the processor 34.

In the processor 34, the heart sound and two pulse wave signals are received, the marker signal of the heart sound signal is first detected, data of 25000 points from the detection of the marker signal is then picked up, the lowest points, the highest points, and 1/5 points of the pulse wave amplitudes, and the time difference to between the 1/5 points, are detected for the two pulse waves based on the picked-up 25000 point data, the data of 25000 points is normalized to assign the values of minus 30000 and plus 30000 for the lowest and the highest amplitudes of the pulse waves, so that the direct current components of the pulse waves are eliminated, and the produced data is transmitted to the processor 36. The 25000 point data corresponds to data of 500 msec for 50 kHz.

In the processor 35, the buffering of the data of the heart sound and the two pulse waves received from processors 32 and 33 is carried out, and after the buffering, the data is transmitted to the waveform display 41 in the display portion 4.

In the processor 36, the waveform coincidence processing by the least square method is carried out based on the 1/5 points, and the time difference between 1/5 points with regard to the region of the forward 5000 point data (corresponding to 100 msec), to obtain the transmission time $T_1$ of the pulse wave (the first time waveform coincidence processing). The waveform coincidence processing by the least square method is carried out based on the obtained transmission time $T_1$, to obtain the transmission time $T_2$ of the pulse wave (the second time waveform coincidence processing). The waveform coincidence processing by the least square method is carried out based on the obtained transmission time $T_2$, to obtain the transmission time $T_3$ of the pulse wave (the third time waveform coincidence processing). The transmission velocity of the pulse wave is calculated based on the obtained transmission time $T_3$ and distance L of the measurement of the pulse wave, and the data of the calculated transmission velocity is transmitted to the numerical data display unit 42 in the display portion 4. The data of the lowest and the highest points and 1/5 points of the amplitudes of the pulse waves and the data region information to which the least square method has been applied, and 25000 point data of the heart sounds and the pulse waves, are transmitted to the processor 37.

In the processor 35, the buffering of the heart sound signal and the two pulse wave signals from processors 31, 32, and 33 is carried out, and after the buffering, the signals are transmitted to the waveform display unit 41 in the display portion 4.

In the processor 37, the data received from the processor 36 is transformed into data for display, whereby it is determined whether or not the processing by the processors has been regularly achieved, is made as a graphic display. The transformed data for display is transmitted to the waveform display unit 43 in the display portion 4.

Figure 3:
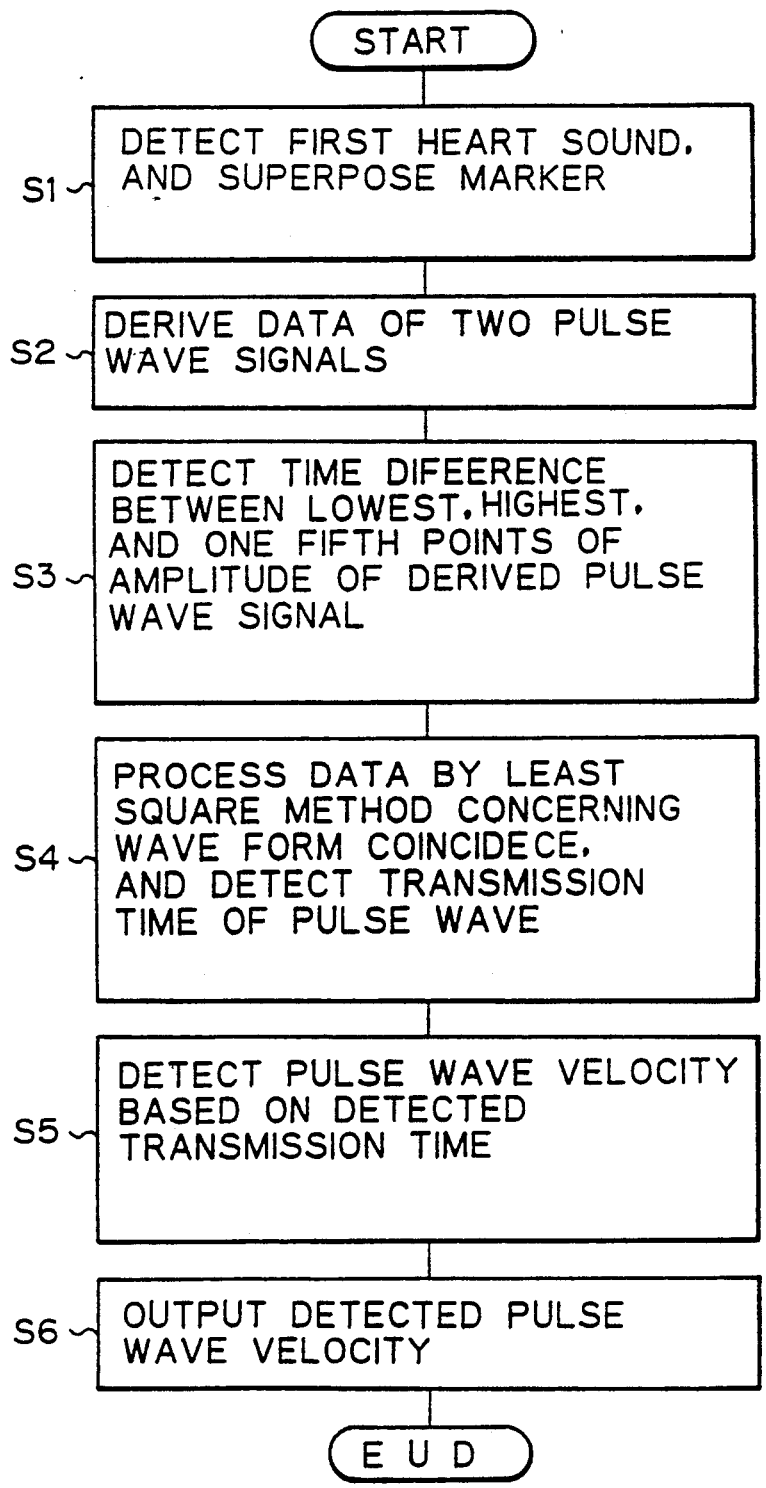
FIG. 3 shows an example of a flow chart of the processing carried out by the data processing unit of the apparatus for measuring the transmission velocity of a pulse wave.

An example of the flow chart of the processing by the data processing portion of the apparatus for measuring transmission velocity of a pulse wave is shown in FIG. 3.

The first of the heart sounds is detected and the marker signal is superposed in step S1; the data of the two pulse wave signals is derived from the marker signal in step S2; the lowest point, the highest point, and 1/5 point of amplitude of the pulse wave, and the time difference between 1/5 points are detected in step S3; the waveform coincidence processing of the data by the least square method is carried out and the transmission time of the pulse wave is detected in step S4; the pulse wave velocity is detected based on the detected transmission time in step S5; and the indication of the detected pulse wave velocity is output in step S6.

Figure 4:
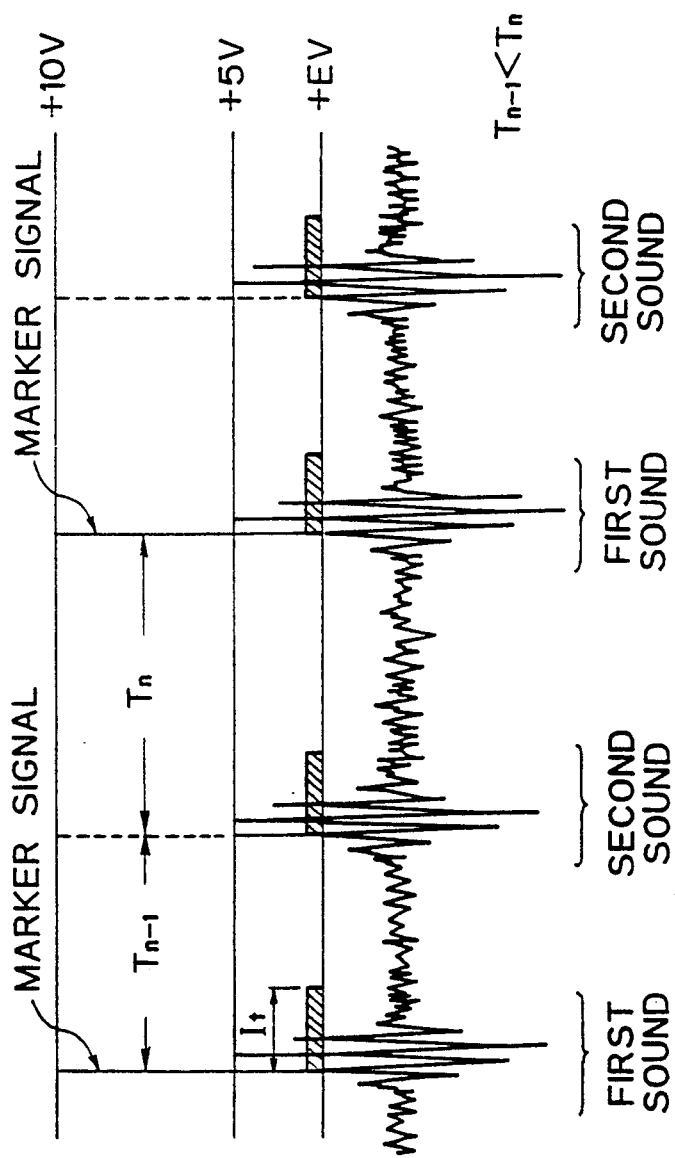
FIG. 4 illustrates an example of the detection of the first of the heart sounds.

An example of the detection of the first of the heart sounds is illustrated in FIG. 4. With regard to the first and the second heart sounds of a human being, the amplitude of the first sound is detected as a large amplitude, and subsequently, the second sound is detected as a large amplitude By using a threshold value E, several points of the first sound group and several points of the second sound group are detected. To detect the first detected point as the first or second point, an inhibition time (It) is provided which is several tens of msec from the relevant detection point, to exclude the remaining points. It is assumed that the first sound is the sound of the closing of the mitral valve in the heart, i.e., the sound of the closing of the valve simultaneously with the charging of the blood from the left atrium into the left ventricle, and the second sound is the sound of the closing the aortic valve when the blood is delivered from the left ventricle into the aorta.

If the time interval $T_n$, between the two successive sounds is greater than $T_{n-1}$ between the immediately preceding two successive sounds, i.e., $T_n > T_{n-1}$, the detected point is determined as the first sound. Conversely, if $T_{n-1} > T_n$, the detected point is determined to be the second sound. This is because the interval between the first sound and the second sound is less than the interval between the second sound and the first sound.

The marker signal, which is a pulse signal having a width of several tens of msec, from the detection point of the first sound is superposed on the original signal. The marker signal is used for checking the waveform on the real time monitor and for information necessary to the subsequent processes. The measurement of time is carried out by a timer in the processors.

To measure the transmission time of the pulse wave, first the 1/5 point and the transmission time of the pulse wave between 1/5 points are detected, and, then the waveform coincidence processes by the least square method are carried out.

Figure 5:
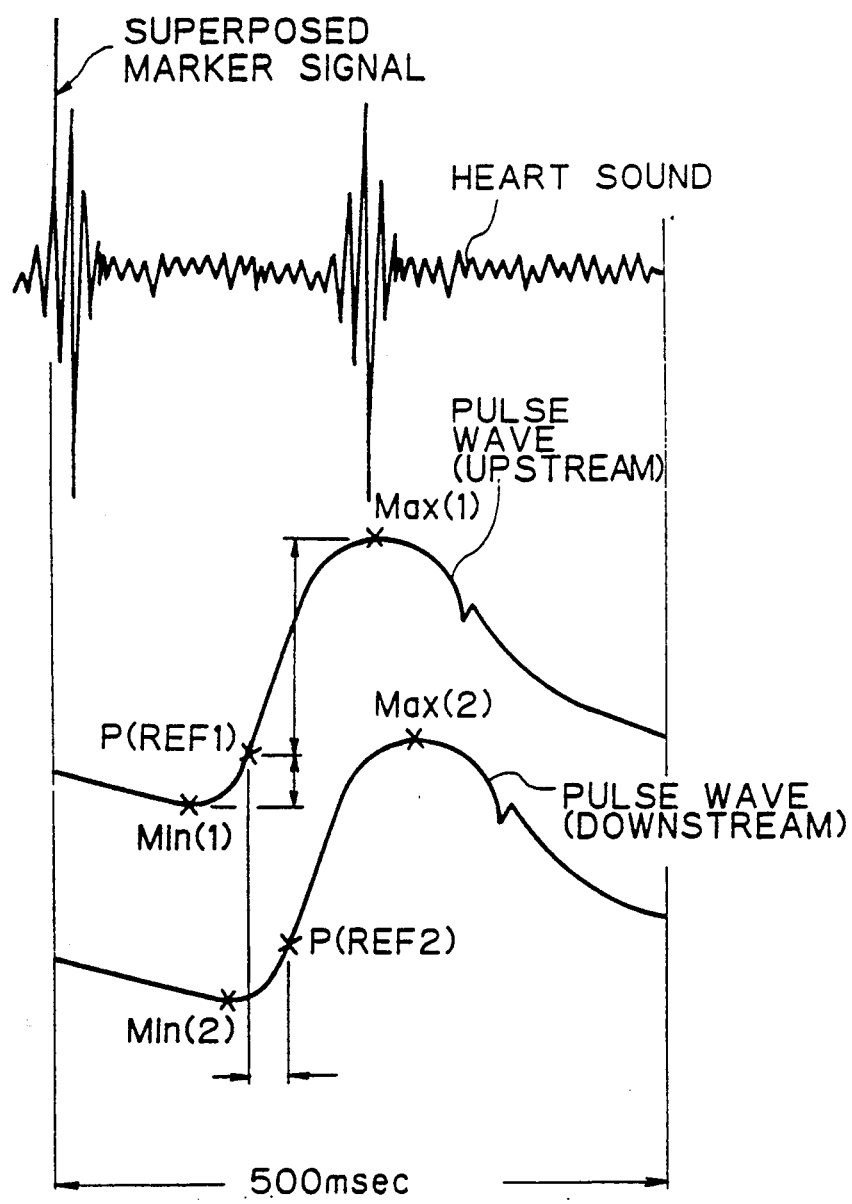
FIG. 5 illustrates an example of the detection of the transmission time of the pulse wave.

An example of the detection of the transmission time of the pulse wave is illustrated in FIG. 5. The marker signal superposed on the first sound of the heart sound is detected, and the data of 500 msec, i.e. data of 25000 points, from the detection of the marker signal is derived. In this region, the lowest points (Min (1), Min (2)) and the highest points (Max (1), Max (2)) of the amplitudes of the two pulse waves are detected, and the point $t_{e1}$ of the 1/5 of the amplitude at the upstream side based on the relationship $$(MAX(1) - MIN(1))/(5 + MIN(1))$$

and the point $t_{e2}$ of the 1/5 of the amplitude at the downstream side based on a similar relationship are detected. The pulse wave transmission time $T_o$ based on the detection of the 1/5 point is obtained from the time difference $t_{e2} - t_{e1}$.

Figure 6:
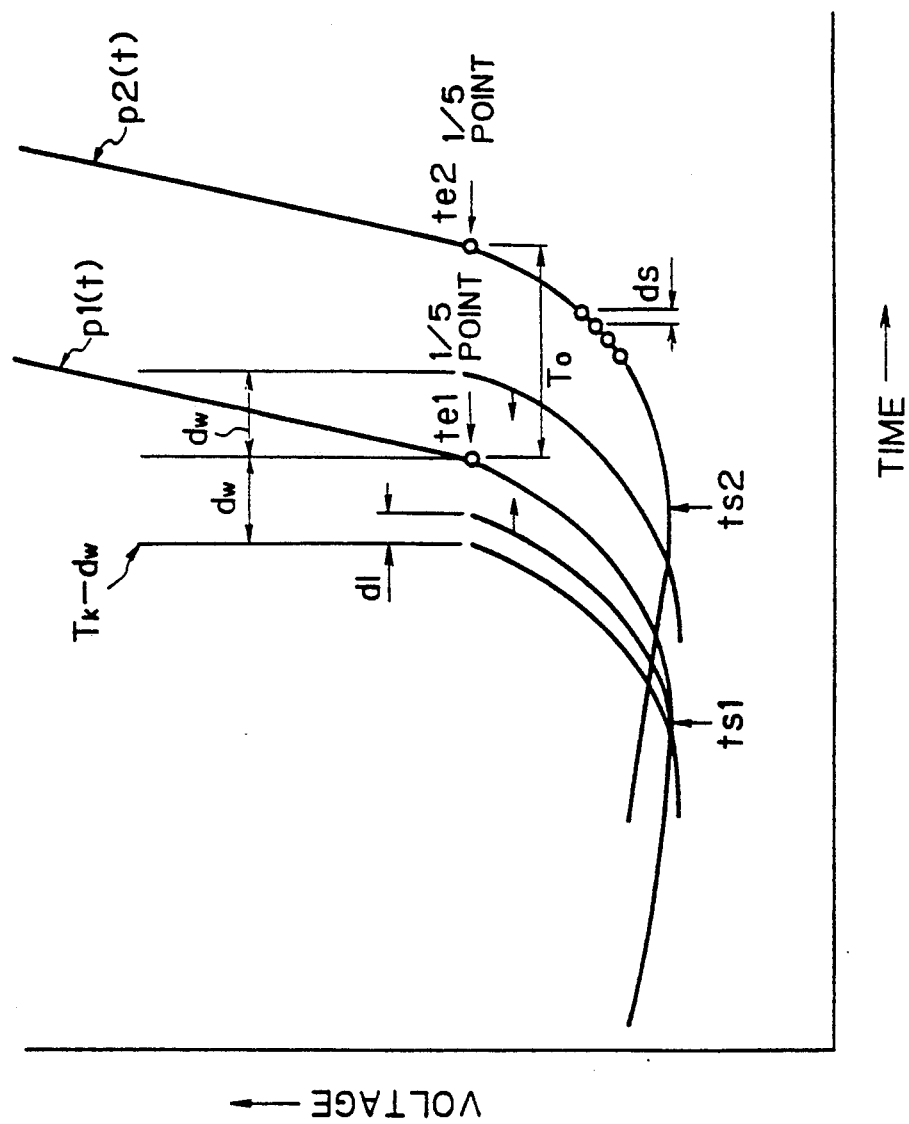
FIG. 6 illustrates an example of the processing of the waveform coincidence.

An example of the processing of the waveform coincidence by the least square method is illustrated in FIG. 6. It is assumed that $t_{e1}$ is the 1/5 point of the amplitude of the pulse wave at the upstream side, $t_{e2}$ is the 1/5 point of the amplitude of the pulse wave at the downstream side, $T_o$ is the estimated value of the transmission time of the pulse wave based on the detection of the 1/5 point, $T_k$ is the estimated value of the transmission time of the pulse wave, ds is the interval of the analysis sampling, di is the time of the analytical chopping of time, and dw is the range of the time of the analysis. Also, it is assumed that n=1, 2, 3, ... 2 dw/di, m=1, 2, 3, ..., k=1, 2, 3, ..., $T_o = t_{e2} - t_{e1}$, $t_{e1} - t_{s1} = 100$ msec, and $t_{e2} - t_{s2} = 100$ msec.

The sum $E_r(n)$ of the squares of the differences between the amplitudes of the pulse waves for the band of the data is calculated, and the transmission time $T_R$ of the pulse wave with regard to the minimum "n" for $E_r(n)$ is derived. It is assumed that:

$$dt = T_{k1} - dw \tag{1}$$

The sum $E_r(n)$ of the squares is given according to the following equation $$E_r(n) = \Sigma(P_1(t_{s2} - dt + di \cdot n + ds \cdot m) - P_2(t_{s2} + ds \cdot m))^2$$

where the summation $\Sigma$ is for from m=1 to $$(T_{e2} - T_{s2})/ds \tag{2}$$

The value of $T_k$ is given according to the following equation:

$$T_k = dt + di \cdot n \tag{3}$$

The operation of the waveform coincidence processing by the least square method is carried out according to the above indicated equations.

First, by using $T_o$, the transmission time $T_1$ of the pulse wave for the first time is obtained under the condition that ds=50, di=100, and dw=400. In this case, 50 corresponds to 1 msec, 100 to 2 msec, and 400 to 8 msec.

Next, by using $T_1$, the transmission time $T_2$ of the pulse wave for the second time is obtained under the condition that ds=10, di=20, and dw=50. In this case, 10 corresponds to 200 μsec, 20 to 400 μsec, and 50 to 1 msec.

Finally, by using $T_2$, the transmission time $T_3$ of the pulse wave for the third time is obtained under the condition that ds=5, di=2, and dw=20. In this case, 5 corresponds to 100 μsec, 2 to 40 μsec, and 20 to 400 μsec.

By using the thus obtained transmission time $T_3$ of the pulse wave, a calculation with the distance L in meters is carried out, to obtain the transmission velocity $V = L/T_3$ of the pulse wave in meters/sec.

Figure 7:
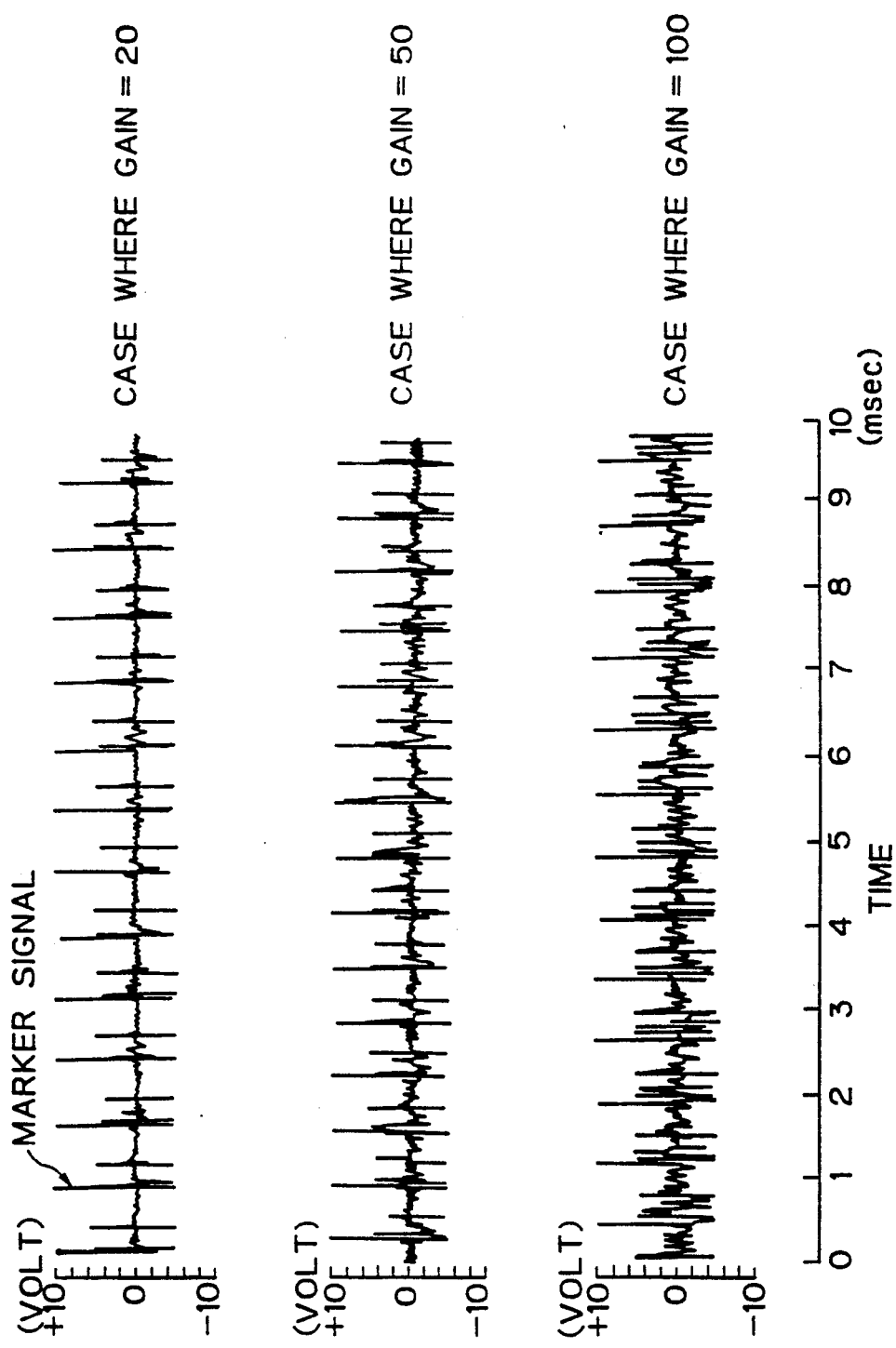
FIG. 7 shows examples of the actual detection of the first of the heart sounds.

Examples of the detection of the first of the heart sounds are illustrated in FIG. 7. The upper waveform shows the case where the gain of the pre-amplifier of the sensor portion is 20, the gain of the middle waveform is 50, and the gain of the lower waveform is 100. It is acknowledged that marker signals are superposed immediately after the detection of the first of the heart sounds, and the first sound is successfully detected.

Figure 8:
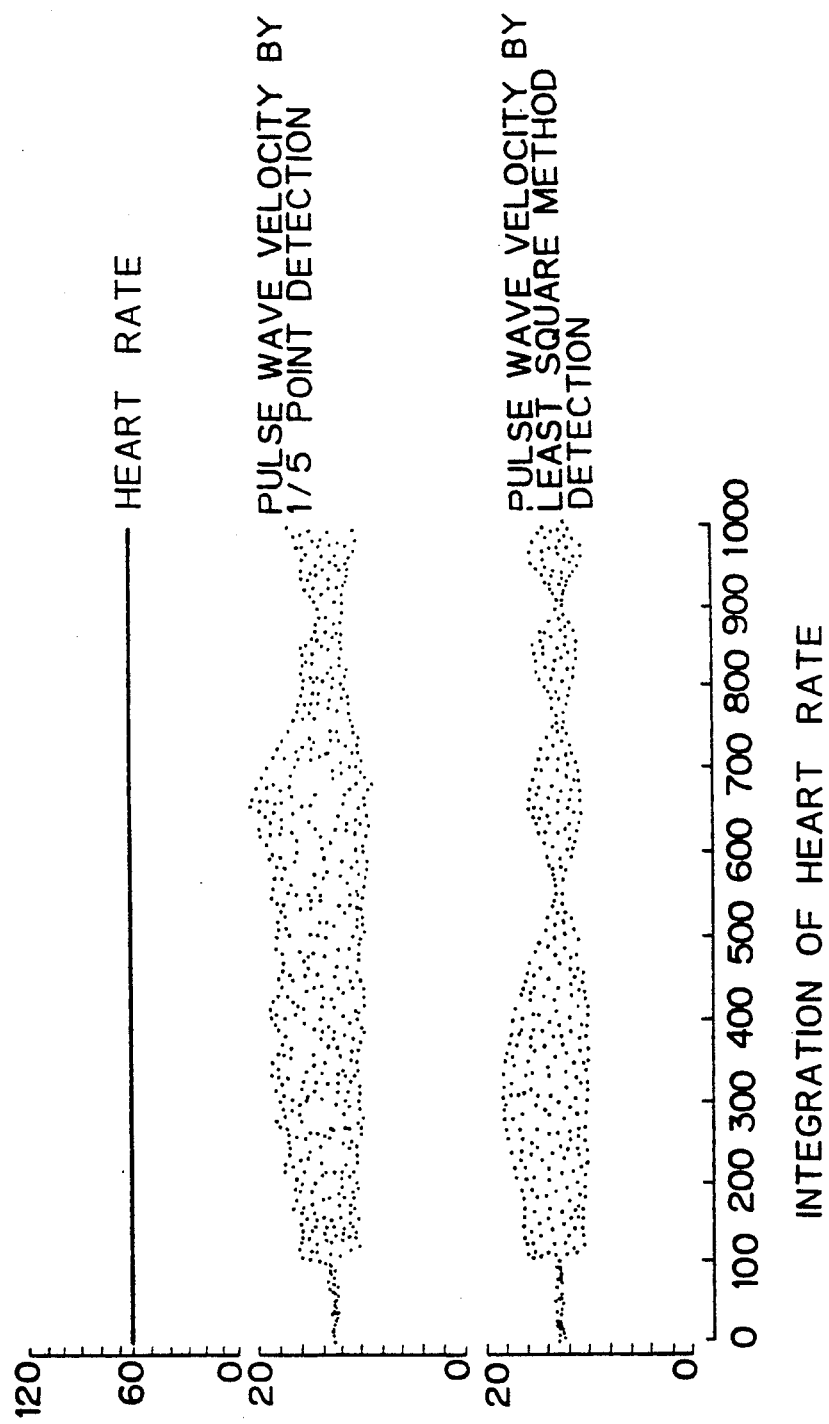
FIG. 8 shows examples of the actual detection of the transmission velocity of the pulse wave.

Examples of the detection of the transmission velocity of the pulse wave are illustrated in FIG. 8. The pulse wave velocity is detected for pulse waves wherein a noise of the sinusoidal waveform type is superposed on pulse waves. In the detection, a simulation signal generated from a simulation signal generator and a noise signal generated from a noise signal generator are used. With the integration of the number of heart beats along the abscissa, first the number of the heart beat, second the pulse wave velocity by the 1/5 point detection, and third, the pulse wave velocity by the least square method detection are illustrated. It is acknowledged that the detected error for the high frequency components of the noise is less in the case of the least square method than in the case of the 1/5 point method.

Examples of the detection of the transmission velocity of the pulse wave are illustrated in FIG. 9. The pulse wave velocity is detected for pulse waves wherein a pseudo random noise is superposed on the pulse waves. A signal having the sinusoidal waveform of the peak-to-peak 100 milli volts from a noise generator is superposed on the pulse wave signal at the downstream side. The measurement is carried out by changing the frequency, the range of the ultimate noise component is limited to 40 Hz by a low pass filter. It is acknowledged that the precision of measurement of the pulse wave velocity is higher in the case of the least square method than in the case of the 1/5 point method.

We claim:

1. An apparatus for measuring a transmission velocity of a pulse wave comprising:

sensor means for sensing heart sounds, and pulse wave signals at upstream and downstream sides of a blood flow;

analog to digital conversion means, coupled to said sensor means, for converting signals from said sensor means from analog to digital form;

data processing means, coupled to said analog to digital conversion means, for processing data received from said analog to digital conversion means; and display means, coupled to said data processing means, for displaying waveforms and numerical data received from said data processing means, wherein said data processing means comprises:

first processor means, coupled to said analog to digital conversion means, for detecting a first heart sound and generating a marker signal;

second and third processor means, coupled to said analog to digital conversion means, for transforming digital signals received from said analog to digital conversion means into data for display;

fourth processor means, coupled to the first, second, and third processor means, for detecting the marker signal from the first processor means and obtaining predetermined data from the data received from said second and third processor means;

fifth processor means, coupled to the second and third processor means, for temporarily storing data received from said second and third processor means;

sixth processor means, coupled to said fourth processor means, for determining a transmission time of a pulse wave to derive a transmission velocity of the pulse wave; and seventh processor means, coupled to said sixth processor means, for transforming signals from the sixth processor means for display.

2. An apparatus according to claim 1, wherein said sensor means comprises a heart sound microphone, a pulse wave pick-up at the upstream side of the blood flow, a pulse wave pick-up at the downstream side of the blood flow, and respective pre-amplifiers, coupled to the microphone and pick-ups, for amplifying signals therefrom and providing the amplified signals to said analog to digital conversion means.

3. An apparatus according to claim 1, wherein said analog to digital conversion means comprises at least one series connection of a filter, a sample and hold circuit, an analog to digital converter, and an interface circuit.

4. An apparatus according to claim 1, wherein said display means comprises waveform display devices for displaying waveforms based on outputs from said fifth and said seventh processor means, and a numerical data display device for displaying numerical data based on output from said sixth processor means.

5. A method of measuring a transmission velocity of a pulse wave, comprising the steps of:
- receiving heart sound signals and pulse wave signals associated with the pulse wave at an upstream and a downstream side of a blood flow;
- detecting a first heart sound from the heart sound signals received in said receiving step;
- obtaining a pulse wave signal at the upstream side of the blood flow and a pulse wave signal at the downstream side of the blood flow based on the first heart sound signal;
- detecting a comparison reference point based on the first heart sound signal and the pulse wave signals at the upstream side of the blood flow and the downstream side of the blood flow;
- performing waveform coincidence processing for the pulse wave signals at the upstream side of the blood flow and the downstream side of the blood flow and, based on the waveform coincidence processing, measuring a transmission time of the pulse wave; and
- deriving a transmission velocity of the pulse wave using the measured transmission time of the pulse wave.

6. A method according to claim 5, wherein the step of detecting the first sound from the heart sound signals, further comprises superimposing a marker signal on the detected first heart sound signal, and, wherein the step of detecting the comparison reference point, further comprises detecting the marker signal.

7. A method according to claim 6, wherein the step of obtaining of the pulse wave signal at the upstream side of the blood flow and at the downstream side of the blood flow further comprises:
- acquiring data within a predetermined length of time from the detection of the marker signal,
- obtaining lowest points and highest points of amplitudes of the pulse waves at the upstream and downstream sides of the blood flow,
- deriving the comparison reference points are derived from the acquired data, and
- obtaining a time difference between the derived comparison reference points is obtained.

8. A method according to claim 7, wherein the measuring of the transmission time further comprises:
- performing a waveform coincidence processing by a least square method for predetermined ranges from the comparison reference points based on the comparison reference points and the time difference therebetween, and
- based on the waveform coincidence processing, measuring the transmission time of the pulse wave.

9. A method according to claim 5, wherein data processing in the method steps is carried out by using a parallel digital data processing system, a real time processing in synchronization with the heart beat being thereby achieved.

* * * * *